US00PP24448P3

(12) United States Plant Patent
Schoone

(10) Patent No.: US PP24,448 P3
(45) Date of Patent: May 13, 2014

(54) ***PHALAENOPSIS* ORCHID PLANT NAMED 'EASTER EGG'**

(50) Latin Name: ***Phalaenopsis* hybrid**
Varietal Denomination: Easter Egg

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 325 days.

(21) Appl. No.: 13/064,525

(22) Filed: Mar. 30, 2011

(65) Prior Publication Data

US 2012/0102605 P1 Apr. 26, 2012

(30) Foreign Application Priority Data

Oct. 20, 2010 (NL) ..... PBR OPS705

(51) Int. Cl.
*A01H 5/00* (2006.01)

(52) U.S. Cl.
USPC ..... Plt./311

(58) Field of Classification Search
USPC ..... Plt./311
See application file for complete search history.

(56) References Cited

U.S. PATENT DOCUMENTS

PP14,266 P3 * 11/2003 van Rijsselberghe ..... Plt./311
PP22,090 P3 * 8/2011 Pen-Chih ..... Plt./311

OTHER PUBLICATIONS

The Santa Barbara Orchid Estate, Orchid of the Day, Jan. 30, 2013 for *Dendrobium delicatum* 'Easter Egg' retrieved from the internet at <http://www.sborchid.com/plantdisplay.php?ooddate=2013-1-30> retrieved Feb. 25, 2013, two pages.*

* cited by examiner

*Primary Examiner* — June Hwu
*Assistant Examiner* — Louanne Krawczewicz Myers
(74) *Attorney, Agent, or Firm* — Foley & Lardner LLP

(57) ABSTRACT

A new and distinct *Phalaenopsis* plant named 'Easter Egg' particularly characterized by flowers which are purple/violet with a white blush in the center; a slightly darker color labellum; plants which may be propagated economically and uniformly using tissue culture; plants which produce more than one inflorescence; long and sturdy inflorescences; and dark-green foliage.

3 Drawing Sheets

Latin name of the genus and species of the plant claimed: *Phalaenopsis* hybrid.

Variety denomination: 'Easter Egg'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Easter Egg'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Easter Egg' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Easter Egg' originated from a cross made by the inventor in 1998 in Strengweg, Heemskerk, The Netherlands. The female or seed parent is the *Phalaenopsis* cultivar designated 'Otohime', unpatented. The male or pollen parent is the *Phalaenopsis* cultivar designated 'Happy Smile', unpatented. The new *Phalaenopsis* 'Easter Egg' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Easter Egg', which in combination distinguish this *Phalaenopsis* as a new and distinct cultivar:

1. flowers which are purple/violet with a white blush in the center; a slightly darker color labellum;
2. plant produces more than one inflorescence;
3. plants may be propagated economically and uniformly using tissue culture;
4. inflorescence is long and sturdy; and
5. relatively short, dark-green foliage.

In comparison with the parental cultivars of 'Easter Egg', the female parent 'Otohime' has pink flowers and the male parent 'Happy Smile' has purple flowers with a very light white blush in the center, whereas the flowers of 'Easter Egg' are purple/violet with a clear white blush in the center.

Presently, the commercial cultivar to which 'Easter Egg' can be meaningfully compared is the *phalaenopsis* orchid 'Heavenly' (unpatented). The height of the plant 'Heavenly' is about 70 cm and there is more white in the flowers, whereas the height of 'Easter Egg' is about 60 cm and there is only a white blush in the center of the flower.

BRIEF DESCRIPTION OF THE PHOTOGRAPHS

The accompanying photographs illustrate the overall appearance of the new *Phalaenopsis* 'Easter Egg' showing the colors as true as is reasonably possible with colored reproductions of this type. Colors in the photographs may differ slightly from the color values cited in the detailed botanical description, which accurately describe the color of 'Easter Egg'.

DETAILED BOTANICAL DESCRIPTION

Figure 1:
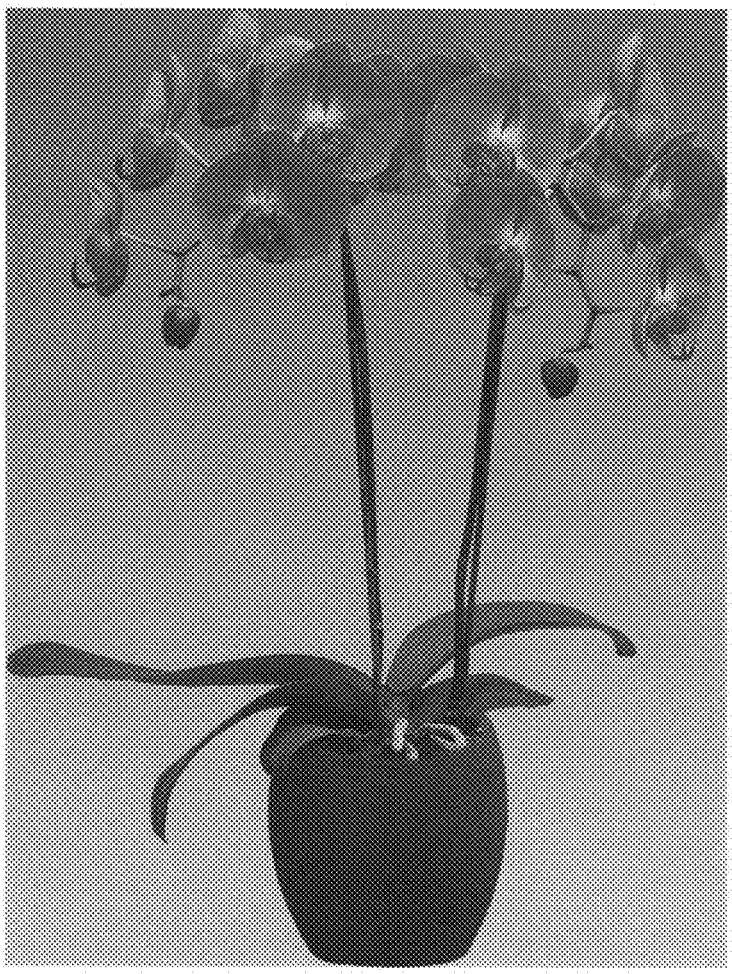
FIG. 1 shows a side view perspective of a typical flowering plant of 'Easter Egg' in a 12 cm pot, at 16 months of age.

The new *Phalaenopsis* cultivar 'Easter Egg' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Easter Egg' as grown in a greenhouse in Strengweg, Heemskerk, The Netherlands, under conditions which closely approximate those generally used in commercial practice. Initially, the ideal temperature to grow plants of 'Easter Egg' is 27° C. during the day and at night. Then, during the flowering phase of 'Easter Egg', the ideal growing temperature is 20-22° C. during the day and 18° C. at night. Light levels for growing 'Easter Egg' are a minimum of 5,000 lux and a maximum of 10,000 lux. A balanced fertilizer with level of 200 ppm N, 87 ppm P, 168 ppm K is applied. Duration of growth of 'Easter Egg' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Easter Egg' plants described is 12 months after potting.

Classification:

*Botanical.*—*Phalaenopsis* hybrid.

Parentage:

*Female or seed parent.*—*Phalaenopsis* cultivar designated 'Otohime', unpatented.

*Male or pollen parent.*—*Phalaenopsis* cultivar designated 'Happy Smile', unpatented.

Propagation:

*Type.*—Tissue culture.

*Rooting habit and description.*—Fleshy; approximately 5 mm-7 mm wide and green in color (RHS 144A); freely branching. It takes 12 weeks for plants growing in tissue culture to initiate roots.

Plant:

*Size at maturity.*—Height (from bottom of pot to the top of the highest flower): about 60 cm. Spread: about 40 cm to 50 cm.

*Growth habit.*—Standard; dark green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture* (*upper & underside*).—Smooth and leathery.

*Pubescence.*—None.

*Mature leaf length.*—About 22 cm.

*Mature leaf width.*—About 9 to 10 cm.

*Mature leaf thickness.*—About 2 mm.

*Mature leaf color.*—Upper side: green (RHS N137B). Under side: yellow/green (RHS 146B).

*Leaf base.*—Acute.

*Margin.*—Entire.

*Venation.*—Pattern: parallel. Color of midvein: upper side: green (RHS N137A). Under side: yellow/green (RHS 146C).

Peduncle:

*Quantity per plant.*—About 1 to 2.

*Number of flowers per raceme.*—About 5 to 15.

*Length.*—About 40 to 60 cm.

*Diameter.*—About 6 mm.

*Strength.*—Strong.

*Aspect.*—Upright.

*Texture.*—Glabrous and smooth.

*Color.*—Brown (RHS 200A) with yellow/green (RHS 146A).

*Internode.*—Length: about 40 mm to 60 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 mm to 22 mm. Diameter (at midpoint): about 13 mm to 19 mm. Shape: egg-shaped/oval. Color: Main color is purple (RHS N79C).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
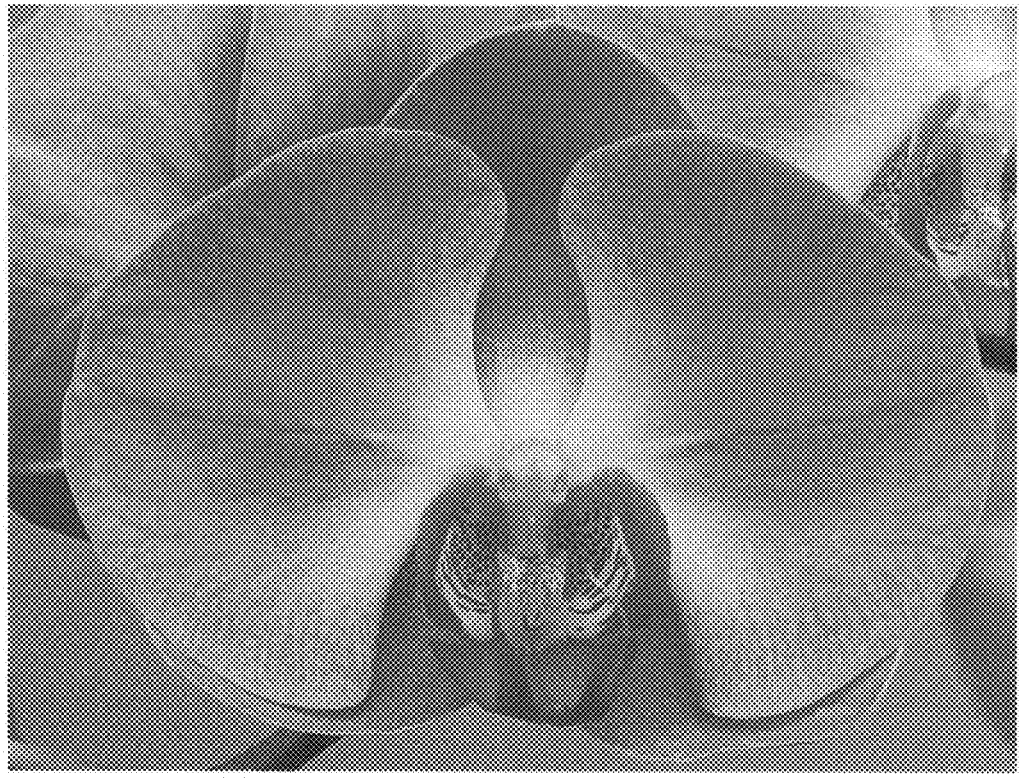
FIG. 2 shows a close-up view of the typical flowers of 'Easter Egg'.
Figure 3:
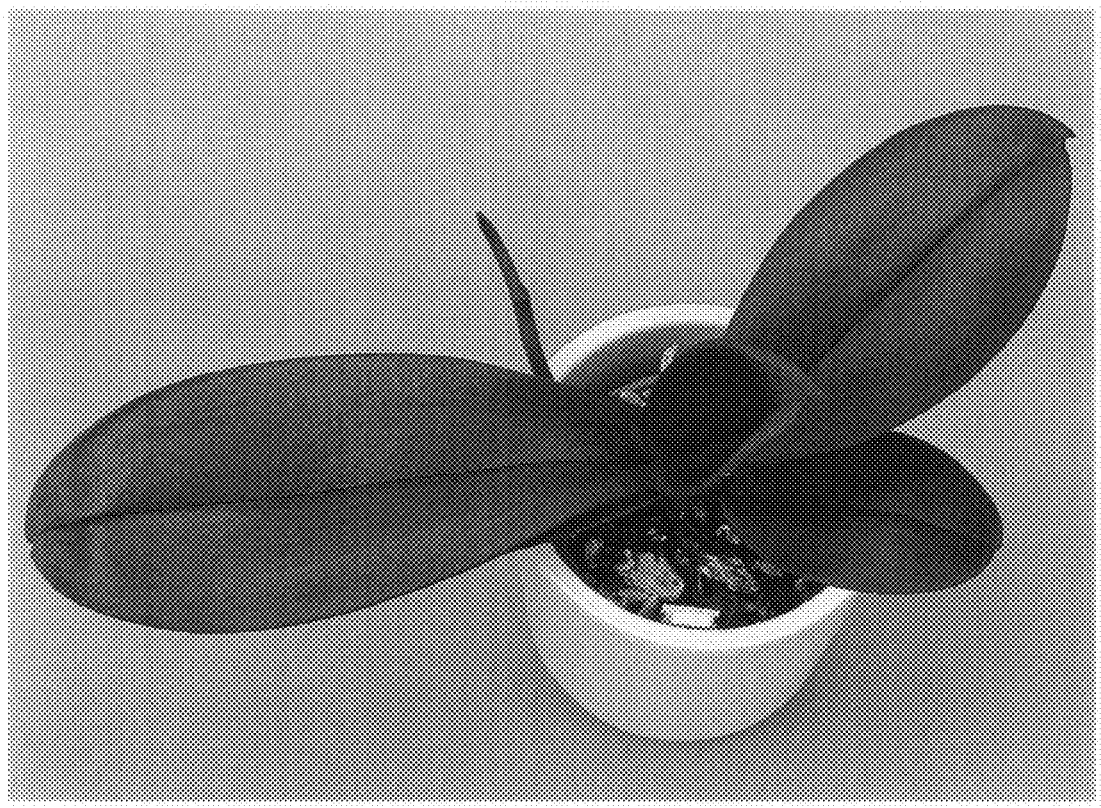
FIG. 3 shows a close-up view of the typical leaves of 'Easter Egg'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 75 mm. Diameter: about 95 mm. Depth of tube: about 15 mm.

*Petals.*—Quantity and arrangement: three petals and three sepals that are trimerous, overlapping and arranged in 2 whorls. Petals are more pronounced than sepals. Arrangement: Inner whorl of petals comprises 3 petals: 2 lateral petals and labellum. 2 lateral petals: Overall shape: broadly ovate and weakly cupped. Apex: oval. Margin: weakly undulate. Base: broadly ovate. Length: about 65 mm. Width: about 45 mm. Texture: Upper surface: smooth and satiny. Under surface: smooth and satiny. Color (when fully opened): Upper side: Main color is purple/Violet (RHS N80B). At the base is a white blush (RHS NN155D). Under side: Main color is RHS N80C with some white at the edges of the base (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 long filiform appendages at the apex. Lateral lobes of the labellum are ovate in shape while the midlobe is triangular with a bump and a rib on it. Margin: entire and weakly undulate. Apex: oval. Length: about 19 mm. Width (not flattened): about 28 mm. Texture: Upper & under surface: smooth and satiny. Color (when fully opened): Midlobe: upper surface: main color of the midlobe is red/purple (RHS 71B) with at the base some yellow (RHS 12A) and at the center and on the edges some red/purple (RHS 60B). Lateral lobes have wide red/purple edges (RHS 71B). Rest is white (RHS NN155C) with some red/purple stripes from base till center (RHS 64A). Under surface: main color of the midlobe and lateral lobes is red/purple (RHS 71C). Base is white (RHS NN155C) with some red/purple stripes (RHS 64B). Cirrhi: about 16 mm long and a bit curly at the end. Color: red/purple (RHS 71B) with white tips (RHS NN155C). Pestle (Callosities): Length: about 4 mm. Width (not flattened): about 3 mm. Color: white on the sides and a little bit inside (RHS NN155C). Edges and top yellow (RHS 12A) with red/purple spots/stripes (RHS 64A).

*Sepals.*—Arrangement: Outer whorl of the flower comprises 3 sepals. Overall shape: elliptical and weakly cupped. Margin: entire and weakly undulate. Base: broadly ovate. Length: about 40 mm. Width: about 34 mm to 39 mm. Apex: oval with small point. Texture: Upper & under surface: smooth and satiny. Color (when fully opened): upper side: The main color is purple/violet (RHS N80B)with at the base some white (RHS NN155D). At the base of the lateral sepals some spots (RHS 71B). Under side: main color is purple/violet (RHS N80C). At the base of the lateral sepals some yellow/green (RHS 145D).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 9 mm. Diameter: about 6 mm. Color: RHS N78C.

*Pollinia.*—Quantity: Two. Diameter: about 1 mm. Color: RHS 17A.

*Ovary.*—Length: about 5 mm. Diameter: about 6 mm to 7 mm. Color: white (RHS NN155C).

*Pedicel.*—Length: about 40 mm tot 60 mm. Diameter: about 4 mm. Texture: glabrous and smooth. Color: green (RHS N137A) to yellow/green (RHS 145C) and red/purple (RHS 59A) to red/purple (RHS 62D).

Disease/pest resistance/susceptibility: No specific resistance or susceptibility observed.

Temperature tolerance: Tolerant to a low temperature of about 15° C. and to a high temperature about 30° C.

The invention claimed is:

1. A new and distinct *Phalaenopsis* plant named 'Easter Egg', as illustrated and described herein.

* * * * *